(12) United States Patent
Poché

(10) Patent No.: US 6,248,730 B1
(45) Date of Patent: *Jun. 19, 2001

(54) ENHANCING THE TOXICITY OF WARFARIN IN RODENTS

(75) Inventor: Richard M. Poché, Wellington, CO (US)

(73) Assignee: Reckittt Benckiser Inc., Wayne, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/243,903

(22) Filed: Feb. 3, 1999

(30) Foreign Application Priority Data

Mar. 9, 1998 (GB) ................................ 9804867

(51) Int. Cl.⁷ .......................... A01N 37/18; A01N 43/16
(52) U.S. Cl. ...................... 514/154; 514/152; 514/457
(58) Field of Search .................. 514/152, 154, 514/457

(56) References Cited

FOREIGN PATENT DOCUMENTS

| | | |
|---|---|---|
| 25 15 639 | 10/1976 | (DE) . |
| 2197514 | 3/1974 | (FR) . |
| 986287 | 3/1965 | (GB) . |

OTHER PUBLICATIONS

Derse, "Anti –K Factor in Anticoagulant Rodenticides, Part II", *Soap & Chem. Specialties*, Apr. 1963 pp. 84–88.
Sulphaquinoxaline—is this the answer to warfarin–resistance?, *Municipal Eng'g*, Mar. 13, 1964, p. 450.
Advertisement for RINOXIN rat and mouse killer (undated, pre–1971).
Qureshi et al., "Warfarin Resistance with Nafcillin Therapy", *Ann. Internal Medicine*, 100:527–529 (1984).
Yacobi et al., Pharmacokinetic and Pharmacodynamic Studies . . . , *J. Pharmacology & Experimental Therapeutics*, 231:72–79 (1984).
Abstract: Yacobi et al., J. Pharmacol. Exp. Ther. 231(1), 72–79 (1984). PCT Ref. XP002103936.
Abstract: Kelly et al., Clin. Pharmacokinet. 4(1), 1–15 (1979). PCT Ref. XP002103937.
Abstract: Remmel et al., Drug Metab. Dispos. 9(5)410–14 (1981). PCT Ref. XP002103938.
Absract: Lechevin, Def. Veg 43 (255–56) 23–27 (1989). PCT Ref. 002103939.

*Primary Examiner*—Allen J. Robinson
(74) *Attorney, Agent, or Firm*—Fish & Richardson P.C.

(57) ABSTRACT

The presence of a small amount of an antibiotic, such as tetracycline or a salt or derivative thereof, in warfarin-containing rodent baits enhances the toxicity of warfarin against rodents which have heretofore shown apparent resistance to warfarin.

6 Claims, No Drawings

ENHANCING THE TOXICITY OF WARFARIN IN RODENTS

FIELD OF THE INVENTION

This invention relates to methods for enhancing the toxicity of warfarin in rodenticidal compositions and to warfarin-containing rodenticidal compositions which are effective against warfarin-resistant rodents.

BACKGROUND OF THE INVENTION

Warfarin, 3-α-phenyl-β-acetylethyl-4-hydroxycoumarin, which has the chemical structure

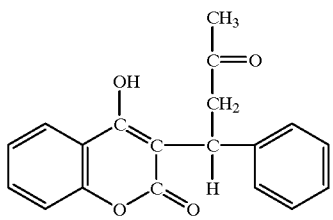

has, since the 1950s been in use as an active ingredient in rodenticidal compositions. In addition to its use as a rodenticide, warfarin is also used, in generally smaller amounts, in humans to provide similar anti-coagulating effects.

The basis for the effectiveness of warfarin as a rodenticide lies in the fact that it is effective in small, multiple doses. One or two doses of the compound are seldom fatal if taken at the recommended concentration; thus the hazard of acute toxicity to man, domestic animals, and wildlife is greatly reduced. In practical use, warfarin has been sold as a "concentrate" containing 0.5 percent of the active ingredient. This is diluted for use with a suitable bait, to a concentration of about 0.025 percent. Baits commonly used are cereal products, corn meal, rolled oats, mixed animal feeds, and similar products. Baits containing warfarin can be placed in stations and left there for considerable periods of time, so that the rodent populations may partake of several doses in sequence. Usually the rodents begin to die after four or five daily doses of the materials, and the population is greatly reduced or eradicated in approximately three weeks. Death is caused by hemorrhages, brought about by the action of the warfarin in reducing the clotting power of the blood. These hemorrhages may be external or internal and can be initiated by very slight injury or capillary damage. One of the other advantages of warfarin is that, because multiple ingestions are required to kill the rodents, they do not develop bait shyness.

Beginning in 1969, rodents— particularly rats and, to a somewhat lesser extent, mice— began showing resistance to warfarin baits. The general assumption was that such resistance had a genetic basis. Similar resistance was found regarding the use of warfarin as an anti-coagulant in treating humans and, to a certain extent, a possible genetic, or at least familial, basis for the decrease in effectiveness of warfarin in treating humans has been substantiated.

As far as warfarin in rodenticides is concerned, the development of resistance has spawned the search for other rodenticidal compounds, including particularly other coumarin derivatives such as flocoumafen, difenacoum and brodifacoum. Brodifacoum currently appears to be the compound of choice in rodenticidal compositions, although others are used. Unfortunately, many of these other compounds also exhibit toxicity toward household pets and therefore use of brodifacoum-containing rodenticidal compositions has to be carefully controlled in a household environment.

As noted above, warfarin, which is often referred to as a "first generation anti-coagulant rodenticide", has the advantage of very low toxicity toward household pets and wildlife and its use does not involve the need to take excessive precautions to avoid contact with household pets or wildlife. Since warfarin has been available for over 40 years and there have been extensive studies of its effectiveness and toxicological properties, it would be extremely advantageous to be able again to use warfarin in commercial rodenticide formulations.

SUMMARY OF THE INVENTION

It has now been discovered that the efficacy of warfarin in rodenticidal compositions can be enhanced by adding an antibiotic to the warfarin-containing composition. A wide range of antibiotics may be used in the practice of this invention and the choice of antibiotic will depend on various factors including availability, cost, etc. Obviously, the antibiotic chosen should be one whose anti-bacterial effectiveness is not weakened by warfarin. An example of an appropriate antibiotic is tetracycline, or one of its salts or one of its derivatives, and the antibiotic should be added in sufficient amount to inhibit the action of bacteria present in the gastrointestinal tract of the rodent.

Accordingly, this invention provides a rodenticidal composition which comprises a rodenticidally effective amount of warfarin and an antibiotic in sufficient amount to inhibit the action of bacteria present in the gastrointestinal tract of the rodent. The antibiotic may be tetracycline, or one of its salts or a derivative thereof. In these compositions, only a relatively small amount of antibiotic is required, generally ranging from about 0.05% to 1.0% based on the weight of the bait.

The invention further provides a method for killing rodents, particularly rats and mice, by causing the rodents to ingest a composition containing a rodenticidally effective amount of warfarin and an antibiotic in an amount sufficient to inhibit the action of bacteria present in the gastrointestinal tract of said rodent. The antibiotic may be tetracycline, or one of its salts or derivatives, or others such as cotrimoxazole, metronidazole, erythromycin, fluconazole, isoniazid, miconazole, ciprofloxacin, and itraconazole.

DETAILED DISCLOSURE

Without wishing to be bound by any scientific theory, it is believed that warfarin "resistance" in rodents may not be true resistance, but rather the result of bacterial action which rapidly metabolizes the warfarin so that the substance no longer acts against the rodents in its customary manner. Reducing the number of bacteria present also significantly reduces the amount of vitamin K available to the rodent. (Vitamin K is an antidote for warfarin.) Thus, the addition of a small amount of an antibiotic agent to the rodenticidal composition has the effect of substantially inhibiting the action of such bacteria, thereby allowing warfarin to metabolize in its usual manner and act as an effective rodenticide. It is therefore not necessary to kill off all of the bacteria which act against warfarin, but only to inhibit such action for sufficient time to enable the warfarin to metabolize normally. Thus, the amount of antibiotic required in the bait composition need only be in the range of, for example, from about 0.05% to 1.0% by weight of the bait compositions. Warfarin used at a level of 0.005–0.05% in said bait compositions is usually sufficiently effective in controlling rodents.

Any antibiotic which acts against the warfarin-inhibiting bacteria is suitable for use in the practice of this invention. These include the well known tricyclic and tetracyclic antibiotics such as tetracycline, its salts and derivatives, for example, tetracycline hydrochloride. Other usable antibiotics include cotrimoxazole, metronidazole, erythromycin, fluconazole, isoniazid, miconazole, itraconazole and ciprofloxacin, as well as their salts and derivatives. The choice of the antibiotic to be used will depend on various factors, including compatibility with other ingredients in the rodenticidal composition, stability, cost, palatability toward the target species, etc. The choice of the particular antibiotic to be employed is well within the knowledge of persons skilled in the art.

Warfarin-containing rodenticidal compositions are typically formulated as granular bait compositions containing from 50–300 ppm, preferably about 250 ppm, of warfarin. The amount of antibiotic to be added to such composition should be from about 0.005 to 0.05% by weight of the warfarin. The bait is typically formulated with from 0.5% to 2.5% of warfarin concentrate in a suitable binder such as corn oil. If corn oil is used as a binder, it can be present in an amount of from about 0.5% to about 2% of the total composition. The binder and warfarin are then mixed in with a grain-based bait composition of the type known in the art. Prior to mixing the composition, an appropriate amount of an antibiotic, such as tetracycline hydrochloride, is added. In addition, an antioxidant may be added to the composition as a preservative for both the warfarin and the antibiotic.

The compositions of this invention may be used for a variety of rodent control products to reduce the population of house mice, rats, field mice, ground squirrels, and other rodents which may be of concern to public health.

EXAMPLE I

A typical formulation has the following constituents:

| Ingredient | % |
| --- | --- |
| Grain carrier | 93.9 |
| Corn oil | 1.0 |
| Warfarin Concentrate (0.5%) | 5.0 |
| Tetracycline hydrochloride | 0.1 |
| Total | 100.0 |

EXAMPLE II

A formulation similar to Example I containing 50 ppm warfarin was tested on groups of warfarin-resistant Norway rats from Chicago, Illinois, and compared against similar formulations without antibiotic. Each group tested had 10 animals. The results are shown in the following table, which contains mortality figures after 5 days of feeding.

| Group | Tetracycline | Mortality |
| --- | --- | --- |
| 1 | Yes | 9/10 |
| 2 | No | 5/10 |

The presence of the antibiotic tetracycline hydrochloride appears to enhance the toxicity of warfarin.

EXAMPLE III

Formulations similar to that of Example I containing tetracycline or metronidazole were tested on groups of Norway rats believed to be warfarin resistant. Each group tested consisting of 8 animals, 4 males and 4 females. Control groups were fed a formulation containing no antibiotic. Other groups were fed formulations containing tetracycline at a concentration of 0.1% (as in Example I) metronidazole at the same concentration.

The test animals were exposed to the warfarin-containing bait for 6 days and observed for another 10-day period. The results are shown in the following table. The column headed "Average Kill Time" is the average number of days which the dead rats survived before dying.

| Group | Antibiotic | Mortality | Average Kill Time |
| --- | --- | --- | --- |
| 3 | none | 5/8 | 6.1 |
| 4 | tetracycline | 7/8 | 6.9 |
| 5 | metronidazole | 7/8 | 7.3 |
| 6 | none | 5/8 | 6.7 |
| 7 | tetracycline | 7/8 | 7.0 |
| 8 | metronidazole | 8/8 | 6.4 |

In addition to the enhanced mortality rates, these data show that the average kill time is not appreciably affected. The fact that the average kill time is not reduced is advantageous in that the addition of antibiotic to the warfarin formulation is not likely to lead to bait shyness among the surviving animals.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

I claim:

1. A method of enhancing the efficacy of warfarin in a rodenticide which comprises adding tetracycline or a salt thereof to a warfarin-containing rodenticidal composition, the amount of said tetracycline or salt being sufficient to inhibit the action of bacteria present in the gastrointestinal tract of a rodent.

2. A method for killing rodents which comprises causing the rodents to ingest a composition comprising an enhanced rodenticidally effective amount of warfarin and tetracycline or a salt thereof in an amount sufficient to inhibit the action of bacteria present and to reduce the amount of vitamin K in the gastrointestinal tract of said rodents.

3. A composition for killing rodents comprising (a) a rodenticidally effective amount of warfarin and (b) tetracycline or a salt thereof in an enhanced effective amount to inhibit the action of bacteria present in the gastrointestinal tract of the rodent.

4. A composition according to claim 3 in which said composition comprises warfarin and tetracycline or a salt thereof suspended in a solid carrier.

5. A composition according to claim 4 in which the tetracycline or a salt thereof is present in an amount of from about 0.05 to 1.0% based on the weight of the composition.

6. A composition according to claim 5 in which warfarin is present in an amount of from about 50 to about 300 ppm.

* * * * *